United States Patent
Ryu et al.

(10) Patent No.: US 9,505,777 B2
(45) Date of Patent: Nov. 29, 2016

(54) METHOD FOR PREPARING ANHYDROUS SUGAR ALCOHOL

(71) Applicant: SAMYANG CORPORATION, Seoul (KR)

(72) Inventors: Hoon Ryu, Daejeon (KR); Young Jae Jung, Daejeon (KR); Jin Kyung Kim, Daejeon (KR); Do Hyun Kyung, Daejeon (KR); Hyuk Min Park, Ganghwa-gun (KR); Seong Ho Cho, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 14/435,630

(22) PCT Filed: Oct. 15, 2013

(86) PCT No.: PCT/KR2013/009196
§ 371 (c)(1),
(2) Date: Apr. 14, 2015

(87) PCT Pub. No.: WO2014/061962
PCT Pub. Date: Apr. 24, 2014

(65) Prior Publication Data
US 2015/0299216 A1    Oct. 22, 2015

(30) Foreign Application Priority Data

Oct. 15, 2012  (KR) .................. 10-2012-0114054

(51) Int. Cl.
| | | |
|---|---|---|
| *B01J 31/02* | (2006.01) | |
| *C07B 63/00* | (2006.01) | |
| *C07D 493/04* | (2006.01) | |

(52) U.S. Cl.
CPC .............. *C07D 493/04* (2013.01); *B01J 31/02* (2013.01); *C07B 63/00* (2013.01)

(58) Field of Classification Search
CPC ....... B01J 31/02; C07B 63/00; C07D 493/04
See application file for complete search history.

(56) References Cited

U.S. PATENT DOCUMENTS

| | | | |
|---|---|---|---|
| 6,639,067 B1 | 10/2003 | Brinegar et al. | |
| 6,670,033 B1 * | 12/2003 | Hubbard | C08G 63/672 428/357 |
| 7,122,661 B2 * | 10/2006 | Fleche | C07D 493/04 536/124 |
| 2002/0052516 A1 * | 5/2002 | Moore | C07D 493/04 549/417 |
| 2003/0097028 A1 * | 5/2003 | Fuertes | C07B 63/04 568/701 |
| 2004/0110969 A1 * | 6/2004 | Fleche | C07D 493/04 549/475 |
| 2007/0213544 A1 * | 9/2007 | Sanborn | C07D 307/02 549/417 |

FOREIGN PATENT DOCUMENTS

| | | |
|---|---|---|
| JP | 2001-102395 A | 4/2001 |
| JP | 2011-51905 A | 3/2011 |
| JP | 2011-102395 A | 5/2011 |
| KR | 2001-0079763 A | 8/2001 |
| KR | 2003-0007926 A | 1/2003 |
| KR | 10-1079518 B1 | 11/2011 |
| KR | 10-2012-0066904 A | 6/2012 |
| KR | WO 2012/081785 * | 6/2012 |
| WO | WO 2005/047228 * | 5/2005 |
| WO | WO 2012/081785 A1 | 6/2012 |

OTHER PUBLICATIONS

International Search Report issued in PCT/KR2013/009196, mailed on Jan. 27, 2014.

* cited by examiner

*Primary Examiner* — Valerie Rodriguez-Garcia
(74) *Attorney, Agent, or Firm* — Birch, Stewart, Kolasch & Birch, LLP

(57) ABSTRACT

The present invention relates to a method for preparing anhydrous sugar alcohol, and more particularly, to a cheap and highly efficient method for preparing anhydrous sugar alcohol having a high final purity of at least 99%, and having good ion content, pH, conductivity, and color properties. According to the method, a hydrogenated sugar is dehydrated so as to be transformed into anhydrous sugar alcohol, and a series of processes including distillation, crystallization, decoloration, and ion exchange resin treatment are conducted.

11 Claims, No Drawings

METHOD FOR PREPARING ANHYDROUS SUGAR ALCOHOL

TECHNICAL FIELD

The present invention relates to a method for preparation of anhydrosugar alcohol, and more specifically a method for preparation of anhydrosugar alcohol through converting hydrogenated sugar to anhydrosugar alcohol by dehydration reaction, and subsequently conducting serial steps of distillation, crystallization, decolorization and treatment with ion exchange resins, by which anhydrosugar alcohol having a final purity of 99% or higher and good properties in all characteristics of ion content, pH, conductivity and color property can be prepared with low cost and high efficiency.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

As such, anhydrosugar alcohol is receiving much interest because of its wide applicability, and the level of practical industrial application thereof is increasing. However, the conventional methods of producing anhydrosugar alcohol have limitations of high cost for the catalyst used in the dehydration reaction, low conversion rate, and low yields of distillation and purification, etc. Furthermore, in various applications of anhydrosugar alcohol as mentioned above, anhydrosugar alcohol is required to have good properties in all characteristics of ion content, pH, conductivity and color property, as well as high purity.

CONTENTS OF THE INVENTION

Problems to be Solved

To resolve the problems of the prior arts as explained above, the present invention has the object of providing a method for preparation of anhydrosugar alcohol by which anhydrosugar alcohol having a final purity of 99% or higher and good properties in all characteristics of ion content, pH, conductivity and color property can be prepared with low cost and high efficiency.

Technical Means

To achieve the above-stated object, the present invention provides a method for preparation of anhydrosugar alcohol comprising the steps of: (1) converting hydrogenated sugar to anhydrosugar alcohol by dehydration reaction; (2) distilling the resulting liquid of the reaction of said step (1); (3) crystallizing the resulting distillate of said step (2); (4) decolorizing the resulting crystallite of said step (3); (5) treating the resulting product of said step (4) with cationic ion exchange resin; and (6) treating the resulting product of said step (5) with anionic ion exchange resin.

Effect of the Invention

According to the present invention, it is possible to produce anhydrosugar alcohol, which has a final purity of 99% or higher and at the same time a remarkably reduced ion content such as 10 ppm or less (more preferably 1 ppm or less; for example, 0.01 to 1 ppm), a proper pH such as 6 to 8, a remarkably low conductivity (the less, the better) such as 10 µS/cm or less (for example, 0.01 to 10 µS/cm) and improved color property such as a yellow index (YI) value of 0.1 or less (for example, 0.01 to 0.1) and is very suitable to be used in various applications, with low cost and high efficiency.

CONCRETE EXPLANATION TO CARRY OUT THE INVENTION

The present invention is explained in more detail below.

[Step (1)] The method for preparation of anhydrosugar alcohol of the present invention comprises a step of converting hydrogenated sugar to anhydrosugar alcohol by dehydration reaction.

The hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials.

As used herein, the expression "anhydrosugar alcohol" means any material that is obtained by removing one or more water molecules from the original inner structure of said hydrogenated sugar in one or more steps by any method.

In the present invention, hexitol is preferably used as the hydrogenated sugar, and more preferably, the hydrogenated sugar for use is selected from sorbitol, mannitol, iditol and mixtures thereof, and even more preferably, sorbitol, which can be prepared easily through hydrogenation reaction of glucose derived from starch, is used.

The hydrogenated sugar is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol.

According to an embodiment of the present invention, for the acid catalyst, a single acid catalyst such as sulfuric acid, nitric acid, hydrochloric acid, p-toluenesulfonic acid, phosphoric acid, etc. can be used, and more preferably, sulfuric acid can be used.

According to another embodiment of the present invention, for the acid catalyst, an acid mixture of a first acid and a second acid can be used, and more preferably, sulfuric acid can be used as the first acid and one or more sulfur-containing acid materials selected from the group consisting of p-toluenesulfonic acid, methanesulfonic acid, ethanesulfonic acid, benzenesulfonic acid, naphthalenesulfonic acid and aluminum sulfate can be used as the second acid.

In case of using an acid mixture, the weight ratio of the first acid:the second acid is preferably from 1:9 to 7:3. If this ratio is less than 1:9 (that is, if the amount of the first acid is relatively too little), the production rate of anhydrosugar alcohol may be lowered. If this ratio is greater than 7:3 (that is, if the amount of the first acid is relatively too great), the generation of sugar polymer may be increased.

The acid catalyst is preferably used in an amount of from 0.5 to 10 parts by weight per 100 parts by weight of the hydrogenated sugar (e.g., hexitol). If the amount of acid catalyst is less than 0.5 part by weight per 100 parts by weight of the hydrogenated sugar, the conversion time to anhydrosugar alcohol may become excessively long. If the amount of acid catalyst is greater than 10 parts by weight, the generation of sugar polymer may be increased and the conversion rate may be lowered.

According to an embodiment of the present invention, the step of converting hydrogenated sugar to anhydrosugar alcohol may be conducted in the presence of an acid catalyst as explained above, at a temperature of from 105° C. to 190° C. under a pressure of 1 to 100 mmHg for 1 hour to 10 hours, but it is not limited thereto.

In the case of using an acid catalyst during the dehydration reaction of hydrogenated sugar, it is preferable to neutralize the reaction product liquid. After the dehydration reaction, the neutralization may be conducted by cooling the reaction product liquid (e.g., to 100° C. or lower) and adding thereto conventional alkali such as sodium hydroxide. The neutralized reaction product liquid preferably has a pH of 6 to 8.

According to a preferable embodiment of the method for preparation of anhydrosugar alcohol of the present invention, the resulting liquid of the step of converting hydrogenated sugar to anhydrosugar alcohol may be pre-treated before being fed to the distilling step. The purpose of the pre-treatment is to remove moisture and a low-boiling-point substance(s) remaining in the resulting liquid of the converting step, and may be conducted by stirring the resulting liquid of the converting step conventionally at a temperature of from 90° C. to 110° C. under a pressure of 10 mmHg to 100 mmHg for 30 minutes or longer (e.g., 30 minutes to 4 hours), but it is not limited thereto.

In the present invention, dianhydrohexitol—which is the dehydrated product of hexitol—is preferably obtained as the anhydrosugar alcohol—which is the product of said conversion reaction—and more preferably, the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

[Step (2)] In the method for preparation of anhydrosugar alcohol of the present invention, the resulting liquid of the reaction of said step (1) is then distilled.

The distilling step can be conducted at a temperature condition of preferably from 100° C. to 250° C., more preferably from 100° C. to 200° C., and still more preferably from 110° C. to 170° C., and under a pressure condition of preferably 10 mmHg or less (e.g., 0.0001 to 10 mmHg, more concretely 0.0001 to 8 mmHg), more preferably 5 mmHg or less (e.g., 0.001 to 5 mmHg), and still more preferably 1 mmHg or less (e.g., 0.01 to 1 mmHg, more concretely 0.01 to 0.8 mmHg). If the distillation temperature is lower than 100° C., the distillation of anhydrosugar alcohol may not be conducted effectively. If the distillation temperature is higher than 250° C., the purity of anhydrosugar alcohol may be lowered and the color will become dark, rendering decolorization difficult. If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to reduce the distillation pressure and the distillation purity would be lowered. If necessary, the distillation may be conducted two or more times. There is no special limitation in the method and device for the distillation, and any conventionally known method and device in this field may be utilized as it is or with proper modification. For example, a general condenser-type evaporator or column distillator may be used, or a thin-film evaporator may be utilized for the distillation.

[Step (3)] In the method for preparation of anhydrosugar alcohol of the present invention, the resulting distillate obtained in said step (2) is then crystallized.

There is no special limitation in the method and device for the crystallization, and any conventionally known crystallization method and device in this field may be utilized as it is or with proper modification. For example, concretely, it is possible to use a method of dissolving anhydrosugar alcohol in a solvent such as water, ethyl acetate, acetone, toluene, benzene, xylene, alcohol, etc. at an elevated temperature if necessary, and then lowering the temperature of the solution to precipitate the anhydrosugar alcohol crystals, or a method of melt crystallization using no solvent may be used. In case of crystallization using solvent, the kind and amount of solvent used and the elevated/lowered temperature, etc. may be determined properly according to the processing capacity and concrete facility conditions, and the temperature condition of melt crystallization may also be determined properly. According to a preferable embodiment of the present invention, acetone is used as a solvent, and after the solvent and the anhydrosugar alcohol distillate are mixed with a weight ratio of from 10:1 to 1:1, the temperature of the solution is elevated to 30° C. or higher and then lowered to 0° C. to precipitate the anhydrosugar alcohol crystals, which are then separated from the mother liquid to obtain the crystallite. In order to improve the total yield of anhydrosugar alcohol, the mother liquid of crystal generated at this time may be concentrated, recovered and then mixed with the resulting liquid of the conversion reaction and again fed into the distilling step. In this case, the distillation yield is improved and thus the effect of improving the total yield can be obtained.

In commercial production of chemical products, it is conventionally recognized that the crystallization is conducted in the last step of the production process in order to increase the purity. However, in the present invention, the crystallization step is disposed directly after the distillation, and subsequently the decolorization and treatment with ion exchange resins are conducted, by which anhydrosugar alcohol satisfying good properties in all characteristics of ion content, pH, conductivity and color property as well as high purity, can be prepared. Furthermore, by employing a process comprising the steps in this specific order, it is possible to reduce the amount of materials necessary for the decolorization and treatment with ion exchange resins (for example, active carbon and ion exchange resins), and in particular, it is possible to obtain the effect of properly adjusting the pH of anhydrosugar alcohol which will become an important factor when the anhydrosugar alcohol is utilized in producing polymers.

[Step (4)] In the method for preparation of anhydrosugar alcohol of the present invention, the resulting crystallite of anhydrosugar alcohol obtained in said step (3) is then decolorized.

Preferably, the decolorization can be conducted by contacting an aqueous solution, where the obtained crystallite of anhydrosugar alcohol is dissolved in water (for example, distilled water), with active carbon. At this time, the average particle size of the active carbon is preferably from 0.25 to 1.0 mm, and more preferably from 0.25 mm to 0.70 mm. If the active carbon particles are so small that the average particle size is less than 0.25 mm, in the case of decolorization on a column the problems of serious decrease of the flow rate and increase of the pressure in the column may result. On the other hand, if the active carbon particles are so large that the average particle size is greater than 1.0 mm, the problems of increase of the ion content and conductivity of the resulting anhydrosugar alcohol and increase of the color index may also result.

There is no special limitation in the manner of contacting the aqueous solution of anhydrosugar alcohol with active carbon. For example, the contact may be conducted in a manner of passing the aqueous solution of anhydrosugar alcohol through a column packed with the active carbon, or it may alternatively be conducted in a manner of incorporating the aqueous solution of anhydrosugar alcohol and the active carbon into a reactor and mixing them with agitation for a given time. According to a preferable embodiment of the present invention, the decolorization is conducted in a manner of passing the aqueous solution of anhydrosugar alcohol through a column packed with the active carbon.

As the active carbon, one or more selected from active carbon groups obtained by activating a plant source such as wooden material, palm, etc. or a mineral source such as brown coal, bituminous coal, soft coal, anthracite coal, etc. may be used. There is no special limitation in the form of active carbon particle, and fine granular active carbon (e.g., average particle size of from 0.25 to 0.75 mm), granular active carbon (e.g., average particle size of 0.75 mm or greater), powder active carbon (e.g., average particle size of 0.25 mm or less), etc. may be used. According to a preferable embodiment of the present invention, fine granular active carbon is used. In order to increase the efficiency of the active carbon, pre-treated (e.g., washed) active carbon may be used.

The requirements for the purity of anhydrosugar alcohol vary according to the application thereof. For food or drug application, impurities harmful to the human body should not be present in anhydrosugar alcohol. For polymer application requiring optical transparency, impurities causing or forming color during synthesis and processing should not be contained in anhydrosugar alcohol. In addition, impurities undesirably increasing or decreasing the degree or rate of polymerization during polymer synthesis should not be contained in anhydrosugar alcohol. In the present invention, anhydrosugar alcohol, which has an increased purity through distillation and crystallization, is decolorized and thereby the above-mentioned impurities can be effectively removed without lowering the purity fundamentally.

[Step (5)] In the method for preparation of anhydrosugar alcohol of the present invention, the decolorized resulting product of said step (4) is then treated with cationic ion exchange resin.

The treatment of the resulting product of step (4) with cationic ion exchange resin may be accomplished by contacting the decolorized resulting liquid with cationic ion exchange resin, and this may be conducted in a manner of passing the decolorized resulting liquid through a column packed with the ion exchange resin. As the cationic ion exchange resin, all of strong cationic ion exchange resin (e.g., TRILITE-SCR-B) and weak cationic ion exchange resin (e.g., DIAION WK11) may be used, and strong cationic ion exchange resin is preferably used. As the strong cationic ion exchange resin, one or more selected from H-form strong cationic ion exchange resin (e.g., TRILITE-SCR-BH) and Na-form strong cationic ion exchange resin (e.g., TRILITE-SCR-B) may be used preferably.

[Step (6)] In the method for preparation of anhydrosugar alcohol of the present invention, the resulting product treated with cationic ion exchange resin of said step (5) is then treated with anionic ion exchange resin.

The contact of the resulting liquid of step (5) with anionic ion exchange resin may be conducted in a manner of passing the resulting liquid of step (5) through a column packed with the ion exchange resin. As the anionic ion exchange resin, all of strong anionic ion exchange resin (e.g., TRILITE AMP24) and weak anionic ion exchange resin (e.g., DIAION WA10) may be used, and strong anionic ion exchange resin is preferably used. As the strong anionic ion exchange resin, Cl-form strong anionic ion exchange resin (e.g., TRILITE AMP24) may be used preferably.

There is no special limitation in the method and column device for the ion purification using ion exchange resin, and any conventionally known method and device in this field may be utilized as it is or with proper modification.

Unlike the above-explained order of ion purification, if the decolorized anhydrosugar alcohol is treated with anionic ion exchange resin and then with cationic ion exchange resin, the resulting product of treatment has a low pH of 3 to 4 and thus a neutralizing agent should be added for its neutralization, by which additional ions are incorporated into the purification product, resulting in an increase of ion content and electric conductivity.

In particular, when anhydrosugar alcohol is used in a process of polymer synthesis or the like, if the anhydrosugar alcohol has a high ion content, control of the polymerization rate becomes difficult. Accordingly, ion content in anhydrosugar alcohol is an important factor in anhydrosugar alcohol application, but conventional methods have not been able to reduce it efficiently. However, the present invention can effectively reduce the ion content in the final product by conducting the above-explained serial processes of treatment with ion exchange resins after the decolorization.

The method for preparation of anhydrosugar alcohol of the present invention may further comprise, if necessary, a step of concentrating or solidifying the anhydrosugar alcohol solution treated with anionic ion exchange resin in said step (6). Through such a concentrating or solidifying step, it is possible to finally obtain the anhydrosugar alcohol product in the shape of flakes or granules.

According to the above-explained method for preparation of anhydrosugar alcohol of the present invention, it is possible to obtain the anhydrosugar alcohol product of high purity and at the same time having remarkably reduced ion content, proper pH, remarkably low conductivity and improved color property.

Thus, according to a preferable embodiment of the present invention, an anhydrosugar alcohol product having a purity of 99% or higher, an ion content of 10 ppm or less (more preferably 1 ppm or less; for example, 0.01 to 1 ppm), a pH of 6 to 8, a conductivity of 10 μS/cm or less (for example, 0.01 to 10 μS/cm) and a yellow index (YI) value of 0.1 or less (for example, 0.01 to 0.1) is provided.

The present invention is explained in more detail through the following Examples and Comparative Examples. However, the Examples are intended to facilitate understanding of the present invention only, and the scope of the present invention is not limited thereby.

EXAMPLES AND COMPARATIVE EXAMPLES

Property Measurement

The purity analysis of anhydrosugar alcohol was carried out by using gas chromatography (GC, HP6890). The ion content analysis was carried out by using an ion chromatograph (Dionex ICS-3000) and the electric conductivity measurement was carried out by using a conductivity meter (Pharmacia Biotech 18-1500). The YI value analysis was carried out by using color spectrometers (Hunterlab Ultrascan vis).

Example 1

1,200 g of sorbitol powder (D-sorbitol, Samyang Genex Inc.) was fed into a four-neck glass reactor equipped with an agitator and melted by heating to 110° C. 12 g of concentrated sulfuric acid (Duksan Chemical, 95%) and 7.2 g of methanesulfonic acid (Sigma, 70%) were added thereto, and the reaction mixture was heated to 135° C. In maintaining this temperature, dehydration reaction was conducted for 4 hours under a vacuum condition of 40 torr to convert the starting material, sorbitol, to the anhydrosugar alcohol, isosorbide. After the dehydration reaction, the reaction mixture was cooled to 110° C., and 31.2 g of 50% sodium hydroxide solution (Samjeon Pure Chemical) was added thereto to neutralize the resulting reaction liquid.

The neutralized anhydrosugar alcohol was distilled by using a thin-film evaporator at 180° C. under vacuum of 5 torr or less. The purity of the obtained anhydrosugar alcohol distillate was 97.5%.

The obtained distillate was placed in a jacketed reaction bath and 300 g of acetone (Samjeon Pure Chemical) was added thereto, and the crystallization was carried out in cooling the mixture to 0° C. After the crystallization was finished, the anhydrosugar alcohol crystals were separated from the mother liquid and recovered.

The obtained crystals were dissolved by adding distilled water thereto, and a solution with solid content of 37% was prepared. The prepared solution was decolorized by passing it through a column packed with fine granular active carbon having average particle size of 0.25 mm at the rate of 1.0 BV/h (bed volume/hour), and the decolorized anhydrosugar alcohol was then passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, to obtain the finally purified anhydrosugar alcohol. The obtained anhydrosugar alcohol showed the final purity of 99.7%.

The finally purified anhydrosugar alcohol was diluted with distilled water to 6% to analyze its ion content. The pH, electric conductivity and YI value of the anhydrosugar alcohol were analyzed and evaluated by diluting it with distilled water to 20%. The analysis results are shown in Table 1 below.

Example 2

The resulting liquid of conversion to anhydrosugar alcohol obtained in Example 1 was first-distilled at 180° C. under 5 torr or less, and the obtained distillate (97.5% purity) was second-distilled at 150° C. under 1 torr or less. At that time, the purity of the distillate was 98.5%. The second distillate (98.5% purity) was purified in the same manner as done in Example 1 with the order of the crystallization, decolorization, cationic ion exchange resin treatment and anionic ion exchange resin treatment. The obtained anhydrosugar alcohol showed the final purity of 99.8%.

The ion content, pH, electric conductivity and YI value of the finally purified anhydrosugar alcohol were analyzed and evaluated in the same manner as in Example 1. The analysis results are shown in Table 1 below.

Comparative Example 1

The resulting liquid of conversion to anhydrosugar alcohol obtained in Example 1 was first-distilled at 180° C. under 5 torr or less, and the obtained distillate (97.5% purity) was dissolved by adding distilled water thereto, and a solution with solid content of 40% was prepared. The prepared solution was decolorized by passing it through a column packed with fine granular active carbon having average particle size of 0.25 mm at the rate of 1.0 BV/h (bed volume/hour), and the decolorized anhydrosugar alcohol was then passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h. The anhydrosugar alcohol solution obtained as such was concentrated to have a moisture content of 1 weight % or less, and the crystallization thereof was carried out in the same manner as in Example 1. The obtained anhydrosugar alcohol showed the final purity of 99.2%.

The ion content, pH, electric conductivity and YI value of the finally purified anhydrosugar alcohol were analyzed and evaluated in the same manner as in Example 1. The analysis results are shown in Table 1 below.

Comparative Example 2

The resulting liquid of conversion to anhydrosugar alcohol obtained in Example 1 was distilled and crystallized in the same manner as in Example 1. The obtained product was used as Comparative Example 2. The obtained anhydrosugar alcohol showed the final purity of 99.5%.

The ion content, pH, electric conductivity and YI value of the finally purified anhydrosugar alcohol were analyzed and evaluated in the same manner as in Example 1. The analysis results are shown in Table 1 below.

Comparative Example 3

The resulting distillate obtained in Example 1 was dissolved by adding distilled water thereto, and a solution with solid content of 37% was prepared. The prepared solution was decolorized by passing it through a column packed with fine granular active carbon having average particle size of 0.25 mm at the rate of 1.0 BV/h (bed volume/hour). After removal of water from the resulting liquid, 300 g of acetone (Samjeon Pure Chemical) was added thereto, and the crystallization was carried out in cooling the mixture to 0° C. After the crystallization was finished, the anhydrosugar alcohol crystals were separated from the mother liquid and recovered. The obtained crystals were dissolved by adding distilled water thereto, and a solution with solid content of 37% was prepared. The prepared solution was passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, to obtain the finally purified anhydrosugar alcohol. The obtained anhydrosugar alcohol showed the final purity of 90.1%.

The ion content, pH, electric conductivity and YI value of the finally purified anhydrosugar alcohol were analyzed and evaluated in the same manner as in Example 1. The analysis results are shown in Table 1 below.

Comparative Example 4

The resulting liquid of conversion to anhydrosugar alcohol obtained in Example 1 was distilled and crystallized in the same manner as in Example 1. The obtained product was dissolved by adding distilled water thereto, and a solution with solid content of 37% was prepared. The prepared solution was passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, and the resulting liquid was then decolorized by passing it through a column packed with fine granular active carbon having average particle size of 0.25 mm at the rate of 1.0 BV/h (bed volume/hour), to obtain the finally purified anhydrosugar alcohol. The obtained anhydrosugar alcohol showed the final purity of 99.7%.

The ion content, pH, electric conductivity and YI value of the finally purified anhydrosugar alcohol were analyzed and evaluated in the same manner as in Example 1. The analysis results are shown in Table 1 below.

Comparative Example 5

The resulting distillate obtained in Example 1 was dissolved by adding distilled water thereto, and a solution with solid content of 37% was prepared. The prepared solution was passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h. After removal of water from the resulting liquid, 300 g of acetone (Samjeon Pure Chemical) was added thereto, and the crystallization was carried out in cooling the mixture to 0° C. After the crystallization was finished, the anhydrosugar alcohol crystals were separated from the mother liquid and recovered. The obtained crystals were dissolved by adding distilled water thereto, and a solution with solid content of 37% was prepared. The prepared solution was decolorized by passing it through a column packed with fine granular active carbon having average particle size of 0.25 mm at the rate of 1.0 BV/h (bed volume/hour), to obtain the finally purified anhydrosugar alcohol. The obtained anhydrosugar alcohol showed the final purity of 99.5%.

The ion content, pH, electric conductivity and YI value of the finally purified anhydrosugar alcohol were analyzed and evaluated in the same manner as in Example 1. The analysis results are shown in Table 1 below.

Comparative Example 6

The resulting distillate obtained in Example 1 was dissolved by adding distilled water thereto, and a solution with solid content of 37% was prepared. The prepared solution was passed through a column packed with H-form strong cationic ion exchange resin (TRILITE-SCR-BH, Samyang Corporation) at the rate of 1.5 BV/h, and the resulting liquid was then passed through a column packed with Cl-form strong anionic ion exchange resin (TRILITE AMP24, Samyang Corporation) at the rate of 1.5 BV/h, and the resulting liquid was then decolorized by passing it through a column packed with fine granular active carbon having average particle size of 0.25 mm at the rate of 1.0 BV/h (bed volume/hour). After removal of water from the resulting liquid, 300 g of acetone (Samjeon Pure Chemical) was added thereto, and the crystallization was carried out in cooling the mixture to 0° C. After the crystallization was finished, the anhydrosugar alcohol crystals were separated from the mother liquid to obtain the finally purified anhydrosugar alcohol. The obtained anhydrosugar alcohol showed the final purity of 99.7%.

The ion content, pH, electric conductivity and YI value of the finally purified anhydrosugar alcohol were analyzed and evaluated in the same manner as in Example 1. The analysis results are shown in Table 1 below.

TABLE 1

| | Final purity | Ion content [1] | pH | Electric conductivity | Color (YI value) |
|---|---|---|---|---|---|
| Example 1 | 99.7% | 0.9 ppm | 7.5 | 1 µS/cm | 0.05 |
| Example 2 | 99.8% | 0.9 ppm | 7.4 | 2 µS/cm | 0.04 |
| Comparative Example 1 | 99.2% | 0.9 ppm | 4.7 | 5 µS/cm | 0.2 |
| Comparative Example 2 | 99.5% | 10 ppm | 4.5 | 18 µS/cm | 1.0 |
| Comparative Example 3 | 90.1% | 4 ppm | 7.6 | 12 µS/cm | 25 |
| Comparative Example 4 | 99.7% | 13 ppm | 7.5 | 25 µS/cm | 0.1 |
| Comparative Example 5 | 99.5% | 12 ppm | 4.9 | 24 µS/cm | 0.1 |
| Comparative Example 6 | 99.7% | 12 ppm | 4.8 | 24 µS/cm | 0.1 |

[1] Ion content: Total of cation content and anion content

As can be seen from Table 1, the anhydrosugar alcohol produced in the Examples of the present invention had high purity and at the same time, remarkably reduced ion content, proper pH, remarkably low conductivity and improved color property. To the contrary, the anhydrosugar alcohol of the Comparative Examples treated differently from the specific order of the present invention showed one or more properties unsatisfied among the evaluated ones. In particular, if anhydrosugar alcohol has a low pH and/or a bad YI value like Comparative Examples 1 to 6, there is a problem of occurrence of yellowing phenomenon during polymer synthesis.

Furthermore, in Comparative Example 3, it was difficult to obtain the desired purity, the crystallization yield was lowered, and the process was complicated, inconvenient and expensive because the dilution and concentration steps had to be conducted two times. In Comparative Example 4, the unit requirements of cationic and anionic resins were increased, and it was difficult to lower the ion content to 1 ppm or less. In Comparative Example 5, the dilution and concentration steps had to be conducted two times, as in Comparative Example 3, and it was difficult to lower the ion content.

The invention claimed is:

1. A method for preparation of anhydrosugar alcohol comprising the steps of:
    (1) converting hydrogenated sugar to anhydrosugar alcohol by dehydration reaction;
    (2) distilling the resulting liquid of the reaction of said step (1) by using a thin-film evaporator;
    (3) crystallizing the resulting distillate of said step (2);
    (4) decolorizing the resulting crystallite of said step (3);
    (5) treating the resulting product of said step (4) with cationic ion exchange resin; and
    (6) treating the resulting product of said step (5) with anionic ion exchange resin,
        wherein no decolorizing is conducted after step (6),
        wherein the decolorization is conducted by using active carbon and wherein the active carbon has an average particle size of from 0.25 mm to 0.75 mm, and
        wherein the prepared anhydrosugar alcohol has as purity of 99% or higher, an on content of 10 ppm or less, a pH of 6 to 8, a conductivity of 10 pS/cm or less, and a YI value of 0.1 or less.

2. The method for preparation of anhydrosugar alcohol according to claim 1, wherein the hydrogenated sugar is hexitol and the anhydrosugar alcohol is dianhydrohexitol.

3. The method for preparation of anhydrosugar alcohol according to claim 1, wherein an acid catalyst is used in the step of converting hydrogenated sugar to anhydrosugar alcohol by dehydration reaction.

4. The method for preparation of anhydrosugar alcohol according to claim 3, wherein the acid catalyst is a single acid catalyst selected from sulfuric acid, nitric acid, hydrochloric acid, p-toluenesulfonic acid and phosphoric acid.

5. The method for preparation of anhydrosugar alcohol according to claim 3, wherein the acid catalyst is an acid mixture of a first acid and a second acid, where the first acid is sulfuric acid and the second acid is one or more sulfur-containing acid materials selected from the group consisting of p-toluenesulfonic acid, methanesulfonic acid, ethanesulfonic acid, benzenesulfonic acid, naphthalenesulfonic acid and aluminum sulfate.

6. The method for preparation of anhydrosugar alcohol according to claim 1, wherein the distillation is conducted two or more times.

7. The method for preparation of anhydrosugar alcohol according to claim 1, wherein the crystallization is conducted by using a solvent.

8. The method for preparation of anhydrosugar alcohol according to claim 1, wherein the crystallization is conducted by a method of melt crystallization.

9. The method for preparation of anhydrosugar alcohol according to claim 1, wherein the cationic ion exchange resin is a strong cationic ion exchange resin.

10. The method for preparation of anhydrosugar alcohol according to claim 1, wherein the anionic ion exchange resin is a strong anionic ion exchange resin.

11. The method for preparation of anhydrosugar alcohol according to claim 1, further comprising the step:
    (7) concentrating or solidifying the resulting product of said step (6).

* * * * *

UNITED STATES PATENT AND TRADEMARK OFFICE
CERTIFICATE OF CORRECTION

PATENT NO. : 9,505,777 B2
APPLICATION NO. : 14/435630
DATED : November 29, 2016
INVENTOR(S) : Hoon Ryu et al.

It is certified that error appears in the above-identified patent and that said Letters Patent is hereby corrected as shown below:

In the Claims

Claim 1, Column 11, Line 40, change "an on content" to --an ion content--.

Claim 1, Column 11, Line 41, change "10 pS/cm" to --10 µS/cm--.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*